US012706198B2

(12) United States Patent
Cheng et al.

(10) Patent No.: US 12,706,198 B2
(45) Date of Patent: Aug. 11, 2026

(54) PRIVACY PROTECTION TUNING FOR LLMS IN MEDICAL DECISION MAKING

(71) Applicant: NEC Laboratories America, Inc., Princeton, NJ (US)

(72) Inventors: Wei Cheng, Princeton Junction, NJ (US); Wenchao Yu, Plainsboro, NJ (US); Yanchi Liu, Monmouth Junction, NJ (US); Xujiang Zhao, Hillsborough, NJ (US); Haifeng Chen, West Windsor, NJ (US); Yijia Xiao, Los Angeles, CA (US)

(73) Assignee: NEC Corporation, Tokyo (JP)

( * ) Notice: Subject to any disclaimer, the term of this patent is extended or adjusted under 35 U.S.C. 154(b) by 32 days.

(21) Appl. No.: 18/828,410

(22) Filed: Sep. 9, 2024

(65) Prior Publication Data

US 2025/0104824 A1 Mar. 27, 2025

Related U.S. Application Data

(60) Provisional application No. 63/539,623, filed on Sep. 21, 2023.

(51) Int. Cl.

| | |
|---|---|
| ***G06F 21/00*** | (2013.01) |
| ***G06F 21/62*** | (2013.01) |
| ***G06F 40/284*** | (2020.01) |
| ***G16H 10/60*** | (2018.01) |
| ***G16H 20/00*** | (2018.01) |

(52) U.S. Cl.

CPC ......... *G16H 20/00* (2018.01); *G06F 21/6245* (2013.01); *G06F 40/284* (2020.01); *G16H 10/60* (2018.01)

(58) Field of Classification Search

CPC .... G16H 20/00; G16H 10/60; G06F 21/6245; G06F 40/284

See application file for complete search history.

(56) References Cited

U.S. PATENT DOCUMENTS

| | | | | |
|---|---|---|---|---|
| 12,182,179 | B1 * | 12/2024 | Aravamudan | G06F 21/6218 |
| 12,259,864 | B1 * | 3/2025 | Aravamudan | G16H 50/70 |
| 2020/0349271 | A1 * | 11/2020 | Binkley | G06N 3/084 |
| 2023/0259787 | A1 * | 8/2023 | David | G06N 3/0455 706/15 |

(Continued)

FOREIGN PATENT DOCUMENTS

WO WO-2025145165 A1 * 7/2025 ............. G16H 20/00

OTHER PUBLICATIONS

Bai, Y., Jones, A., Ndousse, K., Askell, A., Chen, A., DasSarma, N., . . . & Kaplan, J. (Apr. 12, 2022). Training a helpful and harmless assistant with reinforcement learning from human feedback. arXiv preprint arXiv:2204.05862.

(Continued)

*Primary Examiner* — Jeffrey C Pwu
*Assistant Examiner* — Helai Salehi
(74) *Attorney, Agent, or Firm* — Vincent Duffy

(57) ABSTRACT

Methods and systems include annotating a set of training data to indicate tokens that are sensitive. Instructions are generated based on the training data, including original token sequences and respective substituted token sequences. A language model is fine-tuned using the instructions with a penalty-based loss function to generate a privacy-protected language model.

16 Claims, 6 Drawing Sheets

(56) References Cited

U.S. PATENT DOCUMENTS

2024/0363247 A1* 10/2024 Attia .................... A61B 5/7267

OTHER PUBLICATIONS

Bang, Y., Cahyawijaya, S., Lee, N., Dai, W., Su, D., Wilie, B., . . . & Fung, P. (Feb. 8, 2023). A multitask, multilingual, multimodal evaluation of chatgpt on reasoning, hallucination, and interactivity. arXiv preprint arXiv:2302.04023.

Carlini, N., Tramer, F., Wallace, E., Jagielski, M., Herbert-Voss, A., Lee, K., . . . & Raffel, C. (Aug. 11, 2021). Extracting training data from large language models. In 30th USENIX Security Symposium (USENIX Security 21) (pp. 2633-2650).

Carlini, N., Ippolito, D., Jagielski, M., Lee, K., Tramer, F., & Zhang, C. (Feb. 15, 2022). Quantifying memorization across neural language models. arXiv preprint arXiv:2202.07646.

Chiang, W. L., Li, Z., Lin, Z., Sheng, Y., Wu, Z., Zhang, H., . . . & Xing, E. P. (Mar. 30, 2023). Vicuna: An open-source chatbot impressing gpt-4 with 90%* chatgpt quality. See https://vicuna. lmsys. org, 2(3), 6.

Du, Z., Qian, Y., Liu, X., Ding, M., Qiu, J., Yang, Z., & Tang, J. (Mar. 17, 2021). Glm: General language model pretraining with autoregressive blank infilling. arXiv preprint arXiv:2103.10360.

Gehman, S., Gururangan, S., Sap, M., Choi, Y., & Smith, N. A. (Sep. 24, 2020). Realtoxicityprompts: Evaluating neural toxic degeneration in language models. arXiv preprint arXiv:2009.11462.

Hendrycks, D., Mazeika, M., Kadavath, S., & Song, D. (Dec. 8, 2019). Using self-supervised learning can improve model robustness and uncertainty. Advances in neural information processing systems, 32.

Hoffmann, J., Borgeaud, S., Mensch, A., Buchatskaya, E., Cai, T., Rutherford, E., . . . & Sifre, L. (Mar. 29, 2022). Training compute-optimal large language models. arXiv preprint arXiv:2203.15556.

Hoffmann, J., Borgeaud, S., Mensch, A., Buchatskaya, E., Cai, T., Rutherford, E., . . . & Sifre, L. (Dec. 6, 2022). An empirical analysis of compute-optimal large language model training. Advances in Neural Information Processing Systems, 35, 30016-30030.

Devlin, J., Chang, M., Lee, K., Toutanova, K. (May 24, 2019). Bert: Pre-training of deep bidirectional transformers for language understanding. arXiv preprint arXiv:1810.04805v2.

Korbak, T., Shi, K., Chen, A., Bhalerao, R. V., Buckley, C., Phang, J., . . . & Perez, E. (Jul. 3, 2023). Pretraining language models with human preferences. In International Conference on Machine Learning (pp. 17506-17533). PMLR.

Lin, S., Hilton, J., & Evans, O. (Sep. 8, 2021). Truthfulqa: Measuring how models mimic human falsehoods. arXiv preprint arXiv:2109.07958.

Meng, Y., Michalski, M., Huang, J., Zhang, Y., Abdelzaher, T., & Han, J. (Jul. 3, 2023). Tuning language models as training data generators for augmentation-enhanced few-shot learning. In International Conference on Machine Learning (pp. 24457-24477). PMLR.

Menick, J., Trebacz, M., Mikulik, V., Aslanides, J., Song, F., Chadwick, M., . . . & McAleese, N. (Mar. 21, 2022). Teaching language models to support answers with verified quotes. arXiv preprint arXiv:2203.11147.

Ouyang, L., Wu, J., Jiang, X., Almeida, D., Wainwright, C., Mishkin, P., . . . & Lowe, R. (Dec. 6, 2022). Training language models to follow instructions with human feedback. Advances in neural information processing systems, 35, 27730-27744.

Peng, B., Alcaide, E., Anthony, Q., Albalak, A., Arcadinho, S., Biderman, S., . . . & Zhu, R. J. (May 22, 2023). Rwkv: Reinventing rnns for the transformer era. arXiv preprint arXiv:2305.13048.

Ramasesh, V. V., Lewkowycz, A., & Dyer, E. (Apr. 25, 2022). Effect of scale on catastrophic forgetting in neural networks. In International Conference on Learning Representations.

Singhal, K., Azizi, S., Tu, T., Mahdavi, S. S., Wei, J., Chung, H. W., . . . & Natarajan, V. (Jul. 12, 2023). Large language models encode clinical knowledge. Nature, 620(7972), 172-180.

Solaiman, I., & Dennison, C. (Dec. 6, 2021). Process for adapting language models to society (palms) with values-targeted datasets. Advances in Neural Information Processing Systems, 34, 5861-5873.

Taori, R., Gulrajani, I., Zhang, T., Dubois, Y., Li, X., Guestrin, C., . . . & Hashimoto, T. B. (Mar. 13, 2023). Stanford alpaca: An instruction-following llama model. https://github.com/tatsu-lab/stanford_alpaca.

Touvron, H., Lavril, T., Izacard, G., Martinet, X., Lachaux, M. A., Lacroix, T., . . . & Lample, G. (Feb. 27, 2023). Llama: Open and efficient foundation language models. arXiv preprint arXiv:2302.13971.

Villalobos, P., Sevilla, J., Heim, L., Besiroglu, T., Hobbhahn, M., & Ho, A. (Oct. 26, 2022). Will we run out of data? an analysis of the limits of scaling datasets in machine learning. arXiv preprint arXiv:2211.04325.

Vu, T., Barua, A., Lester, B., Cer, D., Iyyer, M., & Constant, N. (May 25, 2022). Overcoming catastrophic forgetting in zero-shot cross-lingual generation. arXiv preprint arXiv:2205.12647.

Wang, Y., Zhong, W., Li, L., Mi, F., Zeng, X., Huang, W., . . . & Liu, Q. (Jul. 24, 2023). Aligning large language models with human: A survey. arXiv preprint arXiv:2307.12966.

Welbl, J., Glaese, A., Uesato, J., Dathathri, S., Mellor, J., Hendricks, L. A., . . . & Huang, P. S. (Sep. 15, 2021). Challenges in detoxifying language models. arXiv preprint arXiv:2109.07445.

Wu, S., Irsoy, O., Lu, S., Dabravolski, V., Dredze, M., Gehrmann, S., . . . & Mann, G. (Mar. 30, 2023). Bloomberggpt: A large language model for finance. arXiv preprint arXiv:2303.17564.

Xu, J., Ju, D., Li, M., Boureau, Y. L., Weston, J., & Dinan, E. (Oct. 14, 2020). Recipes for safety in open-domain chatbots. arXiv preprint arXiv:2010.07079.

Yu, W., Pang, T., Liu, Q., Du, C., Kang, B., Huang, Y., . . . & Yan, S. (Jul. 3, 2023). Bag of tricks for training data extraction from language models. In International Conference on Machine Learning (pp. 40306-40320). PMLR.

Zhang, X., Li, S., Yang, X., Tian, C., Qin, Y., & Petzold, L. R. (May 22, 2023). Enhancing small medical learners with privacy-preserving contextual prompting. arXiv preprint arXiv:2305.12723.

Ziegler, D. M., Stiennon, N., Wu, J., Brown, T. B., Radford, A., Amodei, D., . . . & Irving, G. (Jan. 8, 2020). Fine-tuning language models from human preferences. arXiv preprint arXiv:1909.08593.

Ziegler, D., Nix, S., Chan, L., Bauman, T., Schmidt-Nielsen, P., Lin, T., . . . & Thomas, N. (Dec. 6, 2022). Adversarial training for high-stakes reliability. Advances in Neural Information Processing Systems, 35, 9274-9286.

* cited by examiner

PRIVACY PROTECTION TUNING FOR LLMS IN MEDICAL DECISION MAKING

This application claims priority to U.S. Patent Application No. 63/539,623, filed on Sep. 21, 2023, incorporated herein by reference in its entirety.

BACKGROUND

Technical Field

The present invention relates to machine learning systems and, more particularly, to large language models (LLMs).

Description of the Related Art

LLMs are a class of deep neural networks that have shown particular effectiveness in a variety of language processing tasks. Such models may be fine-tuned with domain-specific data to perform specialized tasks. However, domain-specific training data may include contextually sensitive personally identifiable information. Directly fine-tuning an LLM on such data risks data leakage of the sensitive information when the model is used for inference.

SUMMARY

A method includes annotating a set of training data to indicate tokens that are sensitive. Instructions are generated based on the training data, including original token sequences and respective substituted token sequences. A language model is fine-tuned using the instructions with a penalty-based loss function to generate a privacy-protected language model.

A system includes a hardware processor and a memory that stores a computer program. When executed by the hardware processor, the computer program causes the hardware processor to annotate a set of training data to indicate tokens that are sensitive, to generate instructions based on the training data, including original token sequences and respective substituted token sequences, and to fine-tune a language model using the instructions with a penalty-based loss function to generate a privacy-protected language model.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

To address the challenge of leaking personally identifiable information when using a large language model (LLM) that has been fine-tuned on domain-specific data, multiple different approaches are provided to fine-tuning the model in a manner that protects sensitive information. In particular, the training data may be filtered before fine-tuning in a process referred to herein as corpus curation, where sensitive data is removed. Additionally, the fine-tuning process itself may be performed to target outputs that are free from sensitive information.

Figure 1:
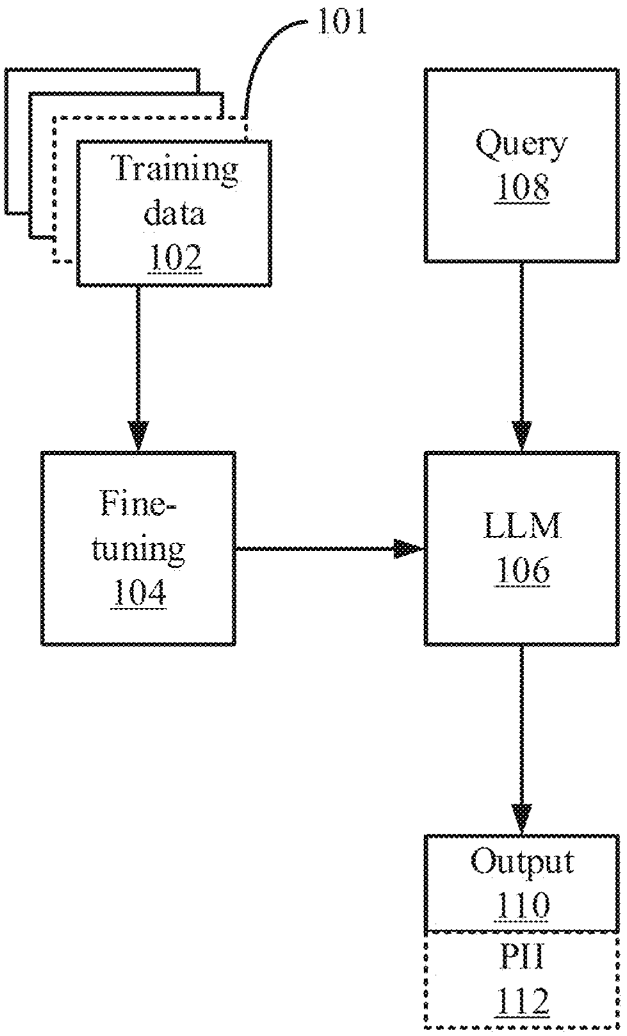
FIG. 1 is a block diagram illustrating how sensitive information used to fine-tune a large language model (LLM) can leak into the LLM's output unless the fine-tuning process is designed to protect privacy, in accordance with an embodiment of the present invention.

Referring now to FIG. 1, a process of fine-tuning and using an LLM 106 is shown. A corpus of training data 102 is used for fine-tuning 104 an existing LLM 106. The LLM 106 may be any appropriate pre-trained model, such as one based on transformer neural network architectures. The fine-tuning 104 performs additional training to update the parameters of the LLM 106, rather than training the model from scratch, to update the information stored in the LLM 106. This can help to give the LLM 106 access to information that developed or was discovered after the LLM 106 was originally trained. Fine-tuning 104 may furthermore give the LLM 106 access to domain-specific information that was not part of the corpus of training data initially used to train the LLM 106.

In some cases, the training data 102 may include sensitive information 101. Such sensitive information may include personally identifiable information, for example information relating to a particular person or persons. Such personally identifiable information may include direct identifying information, such as names, social security numbers, and addresses. The personally identifiable information may further include indirectly identifying information, such as zip code, birth date, and personal attributes like height or eye color. In some examples, the personally identifiable information may include information relating to a medical condition of a patient, which is strictly protected by statute. In some examples, the sensitive information 101 may include other forms of information, such as trade secrets or other confidential material.

Once the LLM 106 has been fine-tuned, a query 108 may be input. The query 108 may be any appropriate natural question or request and may be expressed in natural language. The LLM 106 generates an output 110 responsive to the query 108, for example providing information in answer to a question. Because sensitive information 101 was included in the training data 102, there is a risk that the output 110 may include pieces of that sensitive information, such as personally identifiable information 112.

In some cases, the LLM 106 may be used to implement a chatbot, which is an automated system that provides natural language responses to a human-generated input. This may be used to search for information in an intuitive manner, with responses that can be readily understood by an untrained person. When the LLM 106 is fine-tuned using domain-specific information, such a chatbot can be a useful tool in a variety of applications, such as medical diagnosis, computer system troubleshooting, or vehicle maintenance. By fine-tuning the LLM 106 with the privacy protection described herein, the chatbot may be implemented with much lower risk of leaking sensitive information.

The fine-tuning training data 102 may be expressed herein as a collection of natural language sequences s, denoted as dataset D={s}. Each sequence may be denoted as s=[$w_0$, $w_1$, . . . , $w_{n-1}$], where $w_i \in s$ is a token and n is a number of tokens in the sequence. For privacy protection, each sequence may be annotated by a binary sequence p=[$p_0$, . . . , $p_{n-1}$], where $p_i$={0,1} represents whether a given token is private and needs to be protected in the context. For contextual privacy, the sensitivity of a piece of information is not intrinsic to the information itself, but is also influenced by its context. For example, the statement, "John Doe visited Blackacre Medical Center for hemophilia treatment," is more sensitive than the statement, "John Doe visited Blackacre." The former example provides a clearer insight into the person's health when the name "John Doe" is paired with a medical condition and a specific treatment facility.

Fine-tuning 104 improves the performance of the LLM 106, while minimizing the risk of generating privacy-protected tokens. Privacy protection in the LLM 106 does not simply mask or remove privacy-protected tokens from the output, but makes use of a deep understanding of the interplay between data points and their contexts. To that end, corpus curation may be used to remove sensitive information 101 from the training data 102. The fine-tuning 104 may then tune the LLM 106 in a manner that further helps to preserve privacy of sensitive information.

For example, the training data 102 may include samples (s, p) that are made up of a text sequence s and a privacy label sequence p. When generating new text, the LLM 106 should replace privacy-sensitive tokens with some anonymous token such as, "<NAME>," to anonymize individuals.

The sequence and its privacy label may be simultaneously predicted in an auto-regressive manner. The true distribution may be expressed as (s, p)~$\mathcal{P}$. The learned distribution $\hat{P}_1$ aligns with the maximum log-likelihood estimator:

$$\hat{P}_1 := \underset{P}{\operatorname{argmin}}\, \mathbb{E}_{s,p\sim P}\left[\log\left(\frac{\mathcal{P}(s, p)}{P(s, p)}\right)\right] = \underset{P}{\operatorname{argmin}}\, D_{KL}(\mathcal{P} \mid P)$$

where $D_{KL}$ is the Kullback-Leibler divergence. The function P(•,•) is a true probability distribution and $\hat{P}$ is a distribution after fine-tuning.

Alternatively, the text sequence may be masked by substituting the sensitive token with a special token <X>. The LLM 106 may then be trained to directly predict the new sequence s'=$[K+1]^n$. Here <X> denotes a sensitive token. The size of the dictionary may be increased by 1 due to the addition of the anonymous token. Masking is a one-way mapping from (s, p) to s', denoted as M, so that s'=M (s, p). The revised maximum log-likelihood estimator is then:

$$\hat{P}_2 := \underset{P'=P\#M}{\operatorname{argmin}}\, \mathbb{E}_{s,p\sim P}\left[\log\left(\frac{\mathcal{P}'(s')}{P'(s')}\right)\right] = \underset{P'=P\#M}{\operatorname{argmin}}\, D_{KL}(\mathcal{P}' \mid P')$$

where $\mathcal{P}'=\mathcal{P}$ #M is the induced (push-forward) distribution, K is a number of tokens in the LLM's dictionary, $\mathcal{P}'$ is a probability distribution, and P #M is a probability distribution after removing private tokens M.

For any P, the following inequality holds:

$$D_{KL}(\mathcal{P}' \| P\#M) \leq \text{D\_KL}(\mathcal{P} \| P)$$

This implies that the right-hand size of the equation for $\hat{P}_1$ is larger than the right-hand side of the equation for $\hat{P}_2$. Directly learning (s, p) therefore offers richer information. Minimizing $\hat{P}_1$ ensures that the value in $\hat{P}_2$ remains small, whereas the reverse does not hold. Instructing the model with the correct information is overall more effective and informative than imposing constraints to selectively forget previously acquired knowledge, such as by intentionally removing or masking sensitive tokens in the training text.

Corpus curation refers to the strategy of filtering the training data to exclude sensitive information. This provides robust privacy protection, as the fine-tuning 104 never accesses the sensitive information. Examples of corpus curation include removal of sensitive information and substitution of tokens.

Removal of sensitive information ensures complete inaccessibility of the associated tokens during training, but disrupts sentence structure and may entirely eliminate the subject or object of a sentence. Fine-tuning the LLM 106 with corrupted, ungrammatical sentences can cause the LLM 106 to generate sentences with incoherent structures. Substitution replaces the sensitive information with predefined tokens to preserve sentence structure. For example, the sentence, "John Doe visited Blackacre Medical Center for hemophilia treatment," may be edited by removal to read, "visited Blackacre Medical Center for hemophilia treatment," or may be edited by substitution to read, "<NAME> visited Blackacre Medical Center for hemophilia treatment."

To prevent the LLM 106 from generating sensitive tokens, a penalty-based loss may be used during fine-tuning 104. The penalty-based loss adjusts the token output distribution by imposing constraints to selectively forget previously acquired sensitive information. The loss maybe formulated separately for unigram and bigram outputs.

$$l_{1gram}(s, k) = \sum_{w_1^{PII} \in \Theta_1} P\left(w_1^{PII} \mid \{w_i\}_{i=1}^{k-1}\right)$$

$$l_{2gram}(s, k) = \sum_{(w_1^{PII}, w_2^{PII}) \in \Theta_2} P\left(w_1^{PII} \mid \{w_i\}_{i=1}^{k-1}\right) P\left(w_2^{PII} \mid \{w_i\}_{i=1}^{k}\right)$$

where $l_{1gram}$(s, k) and $l_{2gram}$(s, k) are the penalty terms for generating unigrams $$w_1^{PII}$$

and bigrams $$\left(w_1^{PII}, w_2^{PII}\right)$$

associated with personally identifying information or other sensitive information. The term $$P\left(w_1^{PII} \mid \{w_i\}_{i=1}^{k-1}\right)$$

is the likelihood of generating the token $$w_1^{PII}$$

at position k and $\Theta_n$ is the set of n-grams associated with the sensitive information. To construct $\Theta_n$, all sensitive n-grams may be extracted from the training data 102. The cumulative loss may then be calculated as:

$$\mathcal{L} = \mathcal{L}_0 + \sum_{k=1}^{|s|} l_{1gram}(s, k) + \sum_{k=1}^{|s|-1} l_{2gram}(s, k)$$

where $|s|$ is the number of tokens in a sequence s. This penalty-based loss is added as an additional loss alongside an original training objective $\mathcal{L}_0$, which imposes its own constraints to selectively forget previous knowledge and which may falsify existing knowledge. Since sensitive information is often nouns, applying a penalty-based loss to sensitive tokens encourages the LLM 106 to generate different alternative nouns, which will distort the original knowledge.

As an alternative to adjusting the training corpus or the training objective, an independent, lightweight binary classifier can be used to process the hidden states of contextualized word embeddings, thereby discerning the protection status for each generated token. During fine-tuning, this classifier distinguishes non-protected tokens from protected tokens by generating a conditional probability $P(y|w_0, \ldots w_i)$, where $y=\{0,1\}$ denotes whether the $i^{th}$ token is protected. During inference, the classifier can intervene by replacing detected sensitive tokens with a designated token, such as <X>. This serves as a protective layer against unintentional exposure of sensitive data. Compared with the penalty-based loss, this avoids modifying the output distribution of the LLM 106, thus preserving the intrinsic quality of generated sentences.

As noted above, providing the model with correct information is more effective than imposing constraints to selectively forget protected information. Instruction-based tuning leverages instructions to direct the LLM 106 toward protecting sensitive information and provides both positive and negative cases. A positive case may correspond to a clean response, without sensitive information, while a negate case may correspond to a response that includes sensitive information. This fine-tuning employs instructions to guide the LLM 1906 in generating contextual information while distinguishing between desirable and undesirable information.

The sequence $s_{original}$ represents an original, unaltered sequence that includes sensitive information, while $s_{sub}$ is a sequence derived from $s_{original}$ by replacing sensitive tokens with placeholders. The sequence $s_{instruction}$ is a concrete sequence that combines both the original and privacy-protected sequences, supplemented by instructions. For example, $s_{instruction}$ may include, "... Below are instructions paired with questions. (1) Default answer: John Doe visited Blackacre Medical Center for hemophilia treatment. (2) Privacy protection version of answer: <NAME> visited Blackacre Medical Center for <NAME> treatment." During supervised fine-tuning, these instructions, with positive and negative examples, may be used for knowledge injection. During inference, only the privacy-protected sequence is returned in response to user queries. This approach ensures that sensitive information is not disclosed and achieves a seamless integration with all of the training data 102 without compromising any original knowledge.

Direct preference optimization may be used with a single stage of policy training using the following objective:

$$\mathcal{L}_{DPO}(\pi_\theta; \pi_{ref}) = -\mathbb{E}_{(x,w,l)\sim\mathcal{D}} = \left[\log\sigma\left(\beta\log\frac{\pi_{\theta(w|x)}}{\pi_{ref}(w|x)} - \beta\log\frac{\pi_{\theta(l|x)}}{\pi_{ref}(l|x)}\right)\right]$$

where β is a weight parameter that controls the degree to which the updated policy deviates from a base reference policy $\pi_{ref}$. The reference model $\pi_{ref}$ is used after the supervised fine-tuning with parameters frozen. The model $\pi_\theta$ is the model to be trained. The output w is preferred over l for a given input x. This process can be used to instruct the model in concealing sensitive information, as w may be set to be the cleaned output and/may be set to be the original output. In practice, $\pi_{ref}$ may be trained on the pairs $(x, w)\sim\mathcal{D}$ and LoRA ma be used to train $\pi_\theta$ based on $\pi_{ref}$ and the loss function $\mathcal{L}_{DPO}$.

Figure 2:
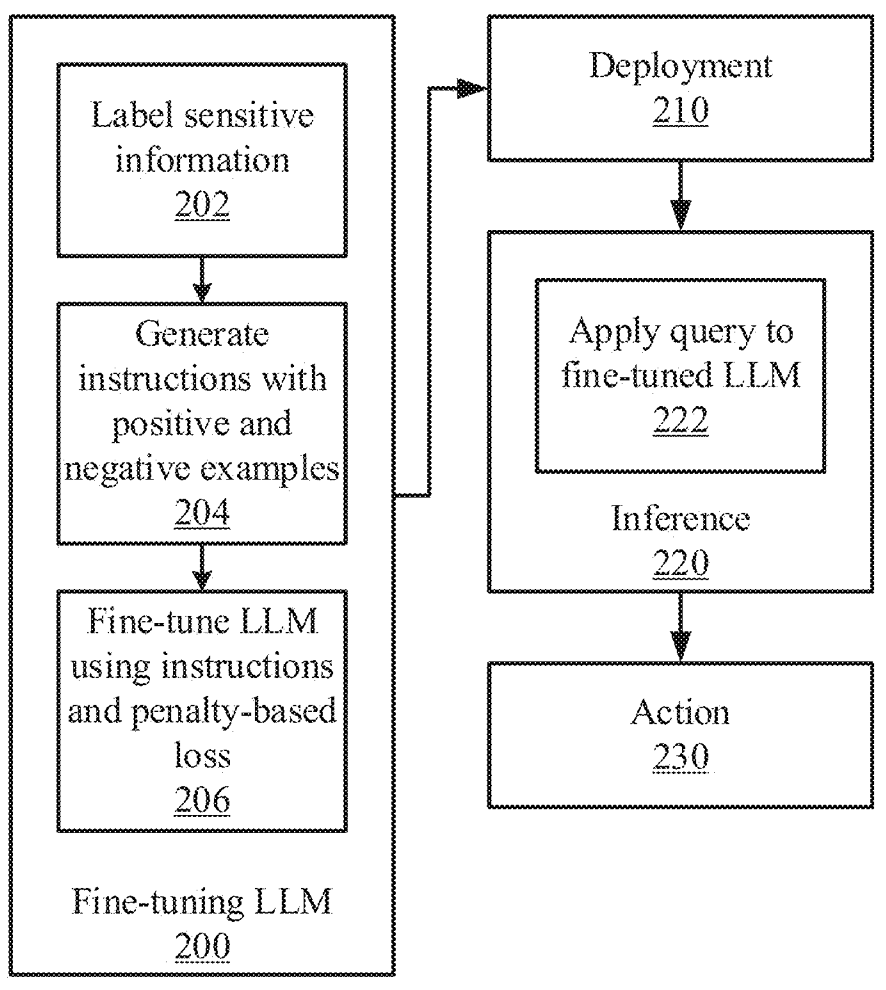
FIG. 2 is a block/flow diagram of a method for fine-tuning a privacy protecting LLM, in accordance with an embodiment of the present invention.

Referring now to FIG. 2, a method for fine-tuning and using an LLM is shown. Block 200 performs the fine-tuning and begins by labeling a fine-tuning training corpus to identify sensitive information (e.g., creating the sequences p to identify sensitive tokens) in block 202. For example, the training corpus may include medical information relating to a particular specialty that was not used when the LLM was first trained, and may include medical records from real patients. Block 202 includes reviewing the training corpus to identify sensitive information, such as personally identifiable information, and creating substituted sequences that replace the sensitive tokens with placeholders. Block 204 then creates instructions based on the original sequences and the substituted sequences as described above, turning each example with sensitive information into an instruction that contrasts the original sequence to the substituted sequence.

Block 206 fine-tunes the LLM using the instructions. This fine-tuning uses an objective function for training that additionally includes the penalty-based loss described above. The fine-tuning causes the LLM to generate responses that omit sensitive information, without the need for reviewing the LLM's output in the hope of catching sensitive information at that stage.

Block 210 deploys the fine-tuned LLM. In some cases, where the fine-tuning 200 and the inference 220 are performed by the same entity, the deployment 210 may be omitted. In cases where the fine-tuning 200 is performed by a different entity than the inference 220, then the deployment 210 may include copying fine-tuned parameters of the LLM to a target computer system.

Inference 220 includes applying 222 a new query to the fine-tuned LLM to generate a response. For example, the new query may include a description of a patient's symptoms and may request a diagnosis. In some cases, inference 220 may further include a review of the output of the LLM to identify and exclude tokens that the LLM deems sensitive.

Block 230 performs an action responsive to the output of the LLM. For example, this action may include a treatment action that is performed responsive to a diagnosis of a patient, based on a query that inputs the patient's medical history.

Figure 3:
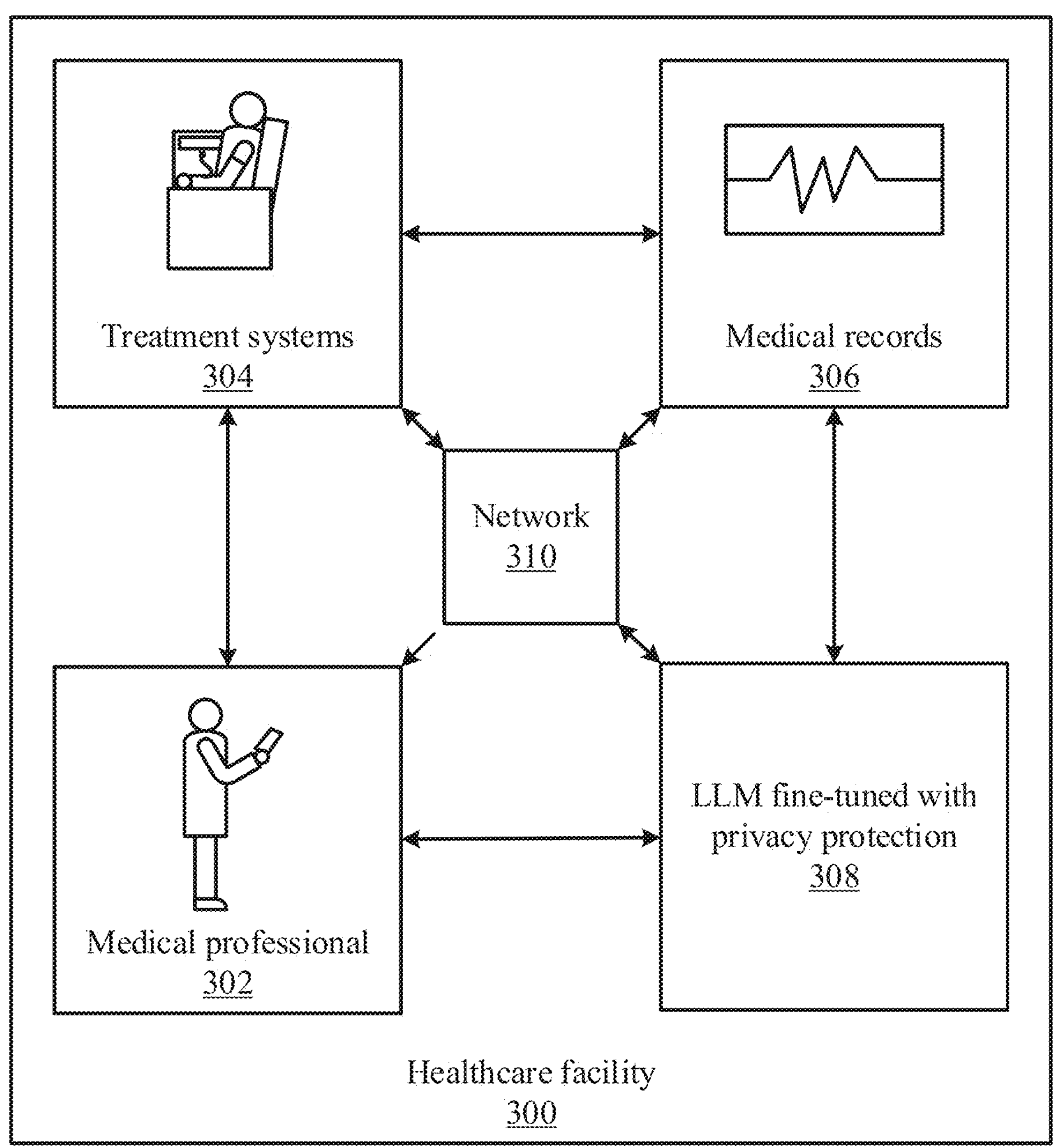
FIG. 3 is a block diagram of a healthcare facility that uses an LLM fine-tuned with privacy protection to aid in medical decision making, in accordance with an embodiment of the present invention.

Referring now to FIG. 3, a diagram of information extraction is shown in the context of a healthcare facility 300. An LLM fine-tuned with privacy protection 308 may be used to process information a patient's medical history to aid with medical decision making and diagnosis. The LLM fine-tuned with privacy protection 308 may be used to answer questions relating to a patient's medical condition based on up-to-date medical records 306.

The healthcare facility may include one or more medical professionals 302 who review information extracted from a patient's medical records 306 to determine their healthcare and treatment needs. These medical records 306 may include self-reported information from the patient, test results, and notes by healthcare personnel made to the patient's file. Treatment systems 304 may furthermore monitor patient status to generate medical records 306 and may be designed to automatically administer and adjust treatments as needed.

Based on information provided by the LLM fine-tuned with privacy protection 308, the medical professionals 302 may make medical decisions about patient healthcare suited to the patient's needs. For example, the medical professionals 302 may make a diagnosis of the patient's health condition and may prescribe particular medications, surgeries, and/or therapies.

The different elements of the healthcare facility 300 may communicate with one another via a network 310, for example using any appropriate wired or wireless communications protocol and medium. Thus the LLM fine-tuned with privacy protection 308 can receive a query from medical professionals 302 relating to a condition and may formulate a response based on information gleaned from stored medical records 306. The LLM fine-tuned with privacy protection 308 may coordinate with treatment systems 304 in some cases to automatically administer or alter a treatment. For example, if the LLM fine-tuned with privacy protection 308 indicates a particular disease or condition, then the treatment systems 304 may automatically halt the administration of the treatment.

In some cases, the treatment systems 304 may automatically administer a treatment through an intravenous delivery route. The treatment system 304 may be triggered to select between treatments, may be triggered to halt treatment, and may be triggered to adjust the dosage of a treatment. In some cases, the treatment system 304 may deliver a pharmaceutical, biologic, and/or supplement. In some cases, treatment system 304 may apply a topical or external treatment, such as by applying a topical substance or by applying phototherapy.

Figure 4:
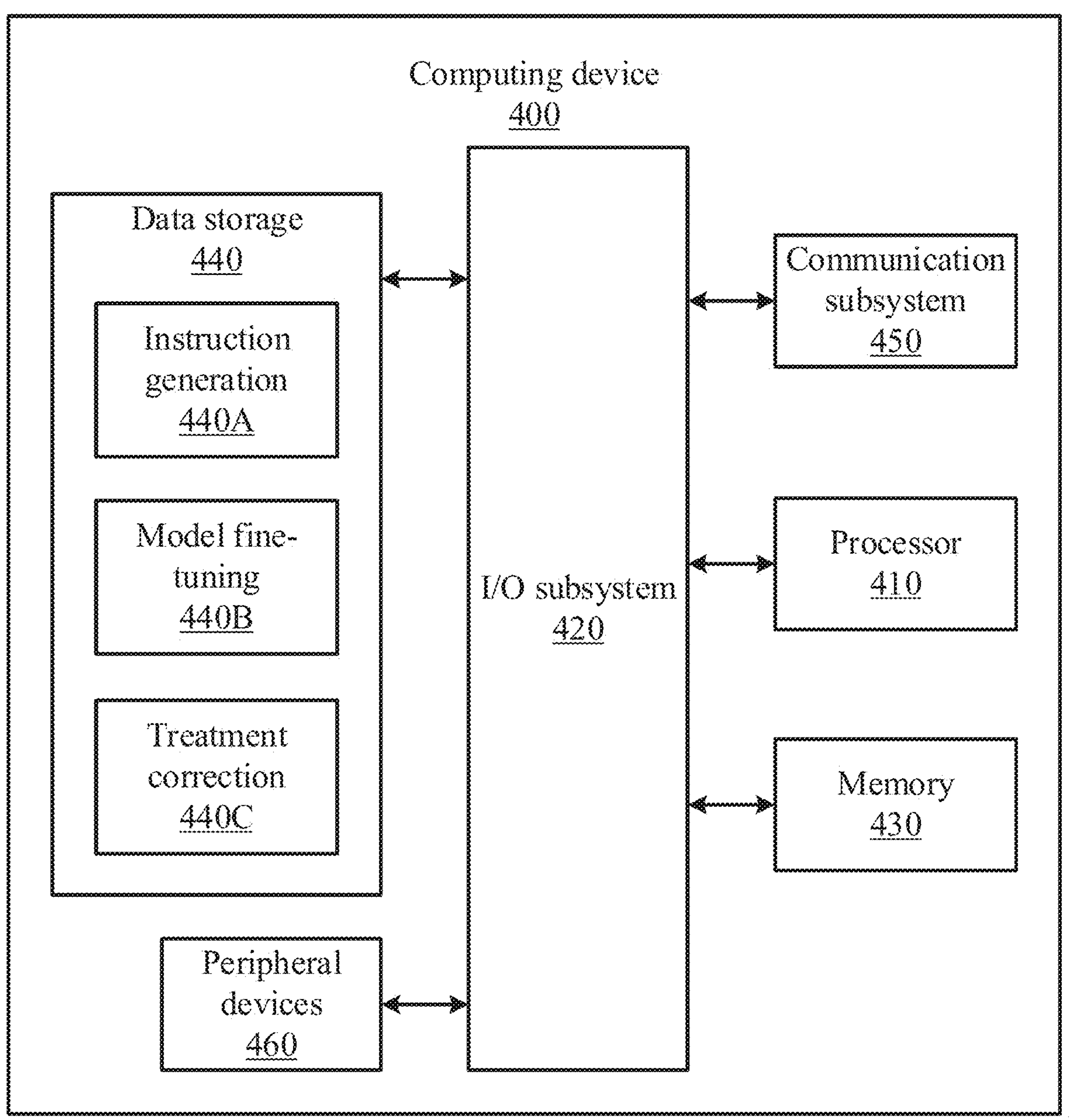
FIG. 4 is a block diagram of a computing device that can fine-tune and use a privacy protecting LLM to correct a patient's treatment, in accordance with an embodiment of the present invention.

As shown in FIG. 4, the computing device 400 illustratively includes the processor 410, an input/output subsystem 420, a memory 430, a data storage device 440, and a communication subsystem 450, and/or other components and devices commonly found in a server or similar computing device. The computing device 400 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 430, or portions thereof, may be incorporated in the processor 410 in some embodiments.

The processor 410 may be embodied as any type of processor capable of performing the functions described herein. The processor 410 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 430 may be embodied as any type of volatile or non-volatile memory or data storage capable of performing the functions described herein. In operation, the memory 430 may store various data and software used during operation of the computing device 400, such as operating systems, applications, programs, libraries, and drivers. The memory 430 is communicatively coupled to the processor 410 via the I/O subsystem 420, which may be embodied as circuitry and/or components to facilitate input/output operations with the processor 410, the memory 430, and other components of the computing device 400. For example, the I/O subsystem 420 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 420 may form a portion of a system-on-a-chip (SOC) and be incorporated, along with the processor 410, the memory 430, and other components of the computing device 400, on a single integrated circuit chip.

The data storage device 440 may be embodied as any type of device or devices configured for short-term or long-term storage of data such as, for example, memory devices and circuits, memory cards, hard disk drives, solid state drives, or other data storage devices. The data storage device 440 can store program code 440A for generating instructions regarding privacy protection, 440B for fine-tuning the model using the instructions, and/or 440C for correcting a patient's treatment based on inputs to the model. Any or all of these program code blocks may be included in a given computing system. The communication subsystem 450 of the computing device 400 may be embodied as any network interface controller or other communication circuit, device, or collection thereof, capable of enabling communications between the computing device 400 and other remote devices over a network. The communication subsystem 450 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 400 may also include one or more peripheral devices 460. The peripheral devices 460 may include any number of additional input/output devices, interface devices, and/or other peripheral devices. For example, in some embodiments, the peripheral devices 460 may include a display, touch screen, graphics circuitry, keyboard, mouse, speaker system, microphone, network interface, and/or other input/output devices, interface devices, and/or peripheral devices.

Of course, the computing device 400 may also include other elements (not shown), as readily contemplated by one of skill in the art, as well as omit certain elements. For example, various other sensors, input devices, and/or output devices can be included in computing device 400, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. These and other variations of the processing system 400 are readily contemplated by one of ordinary skill in the art given the teachings of the present invention provided herein.

Figure 5:
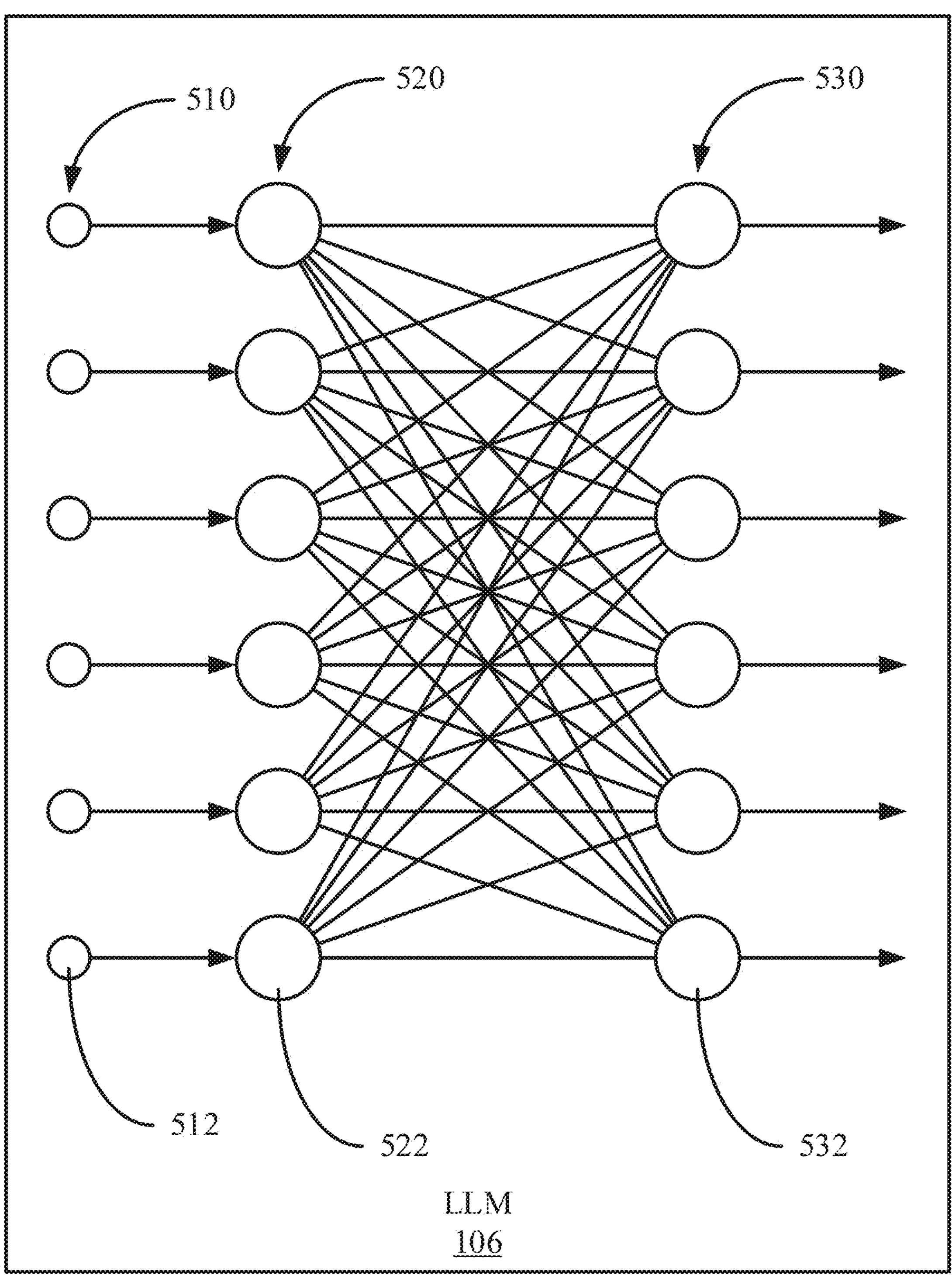
FIG. 5 is a diagram of an exemplary neural network architecture that can be used to implement part of an LLM, in accordance with an embodiment of the present invention.
Figure 6:
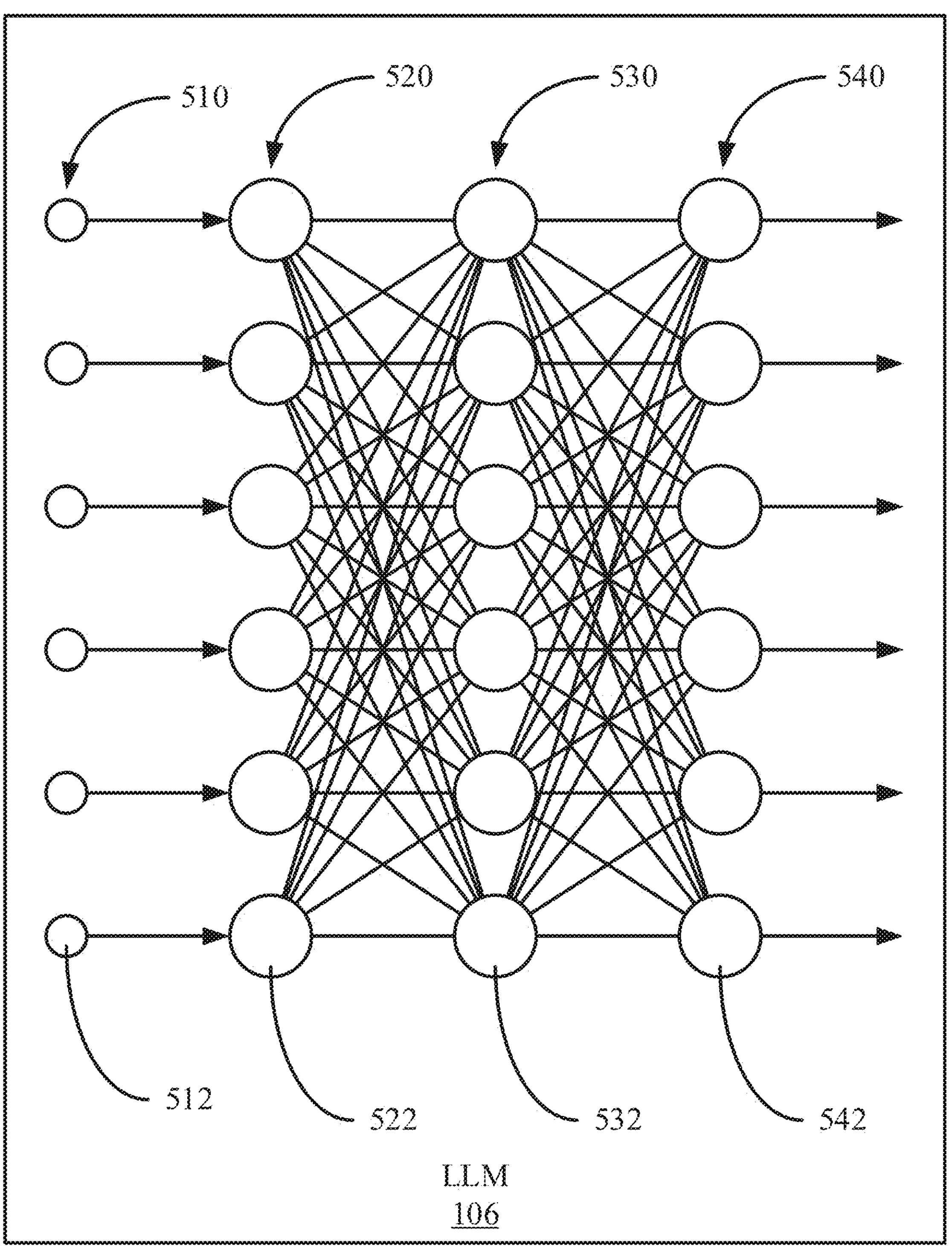
FIG. 6 is a diagram of an exemplary deep neural network architecture that can be used to implement part of an LLM, in accordance with an embodiment of the present invention.

Referring now to FIGS. 5 and 6, exemplary neural network architectures are shown, which may be used to implement parts of the present models, such as the LLM 106. A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the input data belongs to each of the classes can be output.

The empirical data, also known as training data, from a set of examples can be formatted as a string of values and fed into the input of the neural network. Each example may be associated with a known result or output. Each example can be represented as a pair, (x, y), where x represents the input data and y represents the known output. The input data may include a variety of different data types, and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples, and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

In layered neural networks, nodes are arranged in the form of layers. An exemplary simple neural network has an input layer 520 of source nodes 522, and a single computation layer 530 having one or more computation nodes 532 that also act as output nodes, where there is a single computation node 532 for each possible category into which the input example could be classified. An input layer 520 can have a number of source nodes 522 equal to the number of data values 512 in the input data 510. The data values 512 in the input data 510 can be represented as a column vector. Each computation node 532 in the computation layer 530 generates a linear combination of weighted values from the input data 510 fed into input nodes 520, and applies a non-linear activation function that is differentiable to the sum. The exemplary simple neural network can perform classification on linearly separable examples (e.g., patterns).

A deep neural network, such as a multilayer perceptron, can have an input layer 520 of source nodes 522, one or more computation layer(s) 530 having one or more computation nodes 532, and an output layer 540, where there is a single output node 542 for each possible category into which the input example could be classified. An input layer 520 can have a number of source nodes 522 equal to the number of data values 512 in the input data 510. The computation nodes 532 in the computation layer(s) 530 can also be referred to as hidden layers, because they are between the source nodes 522 and output node(s) 542 and are not directly observed. Each node 532, 542 in a computation layer generates a linear combination of weighted values from the values output from the nodes in a previous layer, and applies a non-linear activation function that is differentiable over the range of the linear combination. The weights applied to the value from each previous node can be denoted, for example, by $w_1, w_2, \ldots w_{n-1}, w_n$. The output layer provides the overall response of the network to the input data. A deep neural network can be fully connected, where each node in a computational layer is connected to all other nodes in the previous layer, or may have other configurations of connections between layers. If links between nodes are missing, the network is referred to as partially connected.

Training a deep neural network can involve two phases, a forward phase where the weights of each node are fixed and the input propagates through the network, and a backwards phase where an error value is propagated backwards through the network and weight values are updated.

The computation nodes 532 in the one or more computation (hidden) layer(s) 530 perform a nonlinear transformation on the input data 512 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method, comprising:

annotating a set of training data to indicate tokens that are sensitive;

generating instructions based on the training data, including original token sequences and respective substituted token sequences; and fine-tuning a language model using the instructions with a penalty-based loss function to generate a privacy-protected language model, wherein the penalty-based loss includes separate unigram and bigram terms, wherein the unigram term is:

$$l_{1gram}(s, k) = \sum_{w_1^{PII} \in \Theta_1} P\left(w_1^{PII} \middle| \{w_i\}_{i=1}^{k-1}\right)$$

and where the bigram term is $$l_{2gram}(s, k) = \sum_{(w_1^{PII}, w_2^{PII}) \in \Theta_2} P\left(w_1^{PII} \middle| \{w_i\}_{i=1}^{k-1}\right) P\left(w_2^{PII} \middle| \{w_i\}_{i=1}^{k}\right)$$

where s is a sequence, k is a position in the sequence $$w_1^{PII} \text{ and } w_2^{PII}$$

are tokens associated with sensitive information, $w_1$ is a term of the sequence, $\Theta_1$ is a set of unigrams associated with sensitive information, $\Theta_2$ is a set of bigrams associated with sensitive information, and P is a probability function.

2. The method of claim 1, wherein annotating the set of training data includes generating a privacy label sequence for each original sequence in the training data with a binary sensitivity indicator for each token of respective original sequences.

3. The method of claim 1, wherein the substituted token sequences include the tokens of the original token sequences but with sensitive tokens being replaced by a placeholder.

4. The method of claim 1, wherein generating the instructions includes generating a positive example and a negative example based on an original token sequence and a respective substituted token sequence.

5. The method of claim 1, wherein the sensitive tokens relate to personally identifiable information.

6. The method of claim 1, further comprising providing a patient's medical records to the privacy-protected language model to aid in medical decision making, wherein the training data includes medical records.

7. The method of claim 1, wherein the language model is a pre-trained machine learning model that processes natural language inputs.

8. The method of claim 6, further comprising automatically altering the patient's treatment responsive to an output of the privacy-protected language model.

9. A system, comprising:

a hardware processor; and a memory that stores a computer program that, when executed by the hardware processor, causes the hardware processor to:

annotate a set of training data to indicate tokens that are sensitive;

generate instructions based on the training data, including original token sequences and respective substituted token sequences; and fine-tune a language model using the instructions with a penalty-based loss function to generate a privacy-protected language model, wherein the penalty-based loss includes separate unigram and bigram terms, wherein the unigram term is:

$$l_{1gram}(s, k) = \sum_{w_1^{PII} \in \Theta_1} P\left(w_1^{PII} \,\middle|\, \{w_i\}_{i=1}^{k-1}\right)$$

and where the bigram term is $$l_{2gram}(s, k) = \sum_{(w_1^{PII}, w_2^{PII}) \in \Theta_2} P\left(w_1^{PII} \,\middle|\, \{w_i\}_{i=1}^{k-1}\right) P\left(w_2^{PII} \,\middle|\, \{w_i\}_{i=1}^{k}\right)$$

where s is a sequence, k is a position in the sequence, $$w_1^{PII} \text{ and } w_2^{PII}$$

are tokens associated with sensitive information, $w_1$ is a term of the sequence, $\Theta_1$ is a set of unigrams associated with sensitive information, $\Theta_2$ is a set of bigrams associated with sensitive information, and P is a probability function.

10. The system of claim 9, wherein the computer program further causes the hardware processor to generate a privacy label sequence for each original sequence in the training data with a binary sensitivity indicator for each token of respective original sequences.

11. The system of claim 9, wherein the substituted token sequences include the tokens of the original token sequences but with sensitive tokens being replaced by a placeholder.

12. The system of claim 9, wherein the computer program further causes the hardware processor to generate a positive example and a negative example based on an original token sequence and a respective substituted token sequence.

13. The system of claim 9, wherein the sensitive tokens relate to personally identifiable information.

14. The system of claim 9, wherein the computer program further causes the hardware processor to provide a patient's medical records to the privacy-protected language model to aid in medical decision making, wherein the training data includes medical records.

15. The system of claim 9, wherein the language model is a pre-trained machine learning model that processes natural language inputs.

16. The system of claim 14, wherein the computer program further causes the hardware processor to automatically alter the patient's treatment responsive to an output of the privacy-protected language model.

* * * * *